(12) United States Patent
Lockwood et al.

(10) Patent No.: US 6,685,681 B2
(45) Date of Patent: Feb. 3, 2004

(54) VACUUM THERAPY AND CLEANSING DRESSING FOR WOUNDS

(75) Inventors: Jeffrey S. Lockwood, Batesville, IN (US); Robert Petrosenko, Batesville, IN (US); James Robert Risk, Jr., Milan, IN (US)

(73) Assignee: Hill-Rom Services, Inc., Batesville, IN (US)

(*) Notice: Subject to any disclaimer, the term of this patent is extended or adjusted under 35 U.S.C. 154(b) by 189 days.

(21) Appl. No.: 09/725,352

(22) Filed: Nov. 29, 2000

(65) Prior Publication Data

US 2002/0065494 A1 May 30, 2002

(51) Int. Cl.⁷ ................................................ A61F 13/00
(52) U.S. Cl. ........................... 604/305; 502/43; 502/59
(58) Field of Search .................. 604/289, 304, 604/305, 307, 308, 313, 315, 316, 317, 318, 327, 543; 602/43, 59

(56) References Cited

U.S. PATENT DOCUMENTS

| 774,529 A | 11/1904 | Nieschang |
|---|---|---|
| 1,000,001 A | 8/1911 | Holz |
| 1,355,846 A | 10/1920 | Rannells |
| 1,385,346 A | 7/1921 | Taylor |
| 1,936,129 A | 11/1933 | Fisk |
| 2,195,771 A | 4/1940 | Estler |
| 2,221,758 A | 11/1940 | Elmquist |
| 2,338,339 A | 1/1944 | LeMere et al. |
| 2,443,481 A | 6/1948 | Sene |
| 2,573,791 A | 11/1951 | Howells |

(List continued on next page.)

FOREIGN PATENT DOCUMENTS

| CA | 2303085 | 3/1999 |
|---|---|---|
| DE | 0372727 | 3/1923 |
| DE | 28 09 828 | 9/1978 |
| DE | 3102674 A1 | 9/1982 |
| DE | 3539533 A1 | 5/1987 |
| DE | 4111122 A1 | 4/1993 |
| DE | 0 880 953 A2 | 2/1998 |
| DE | 19722075 C1 | 10/1998 |
| DK | 0064055 | 10/1945 |
| EP | 0424165 A1 | 4/1991 |

(List continued on next page.)

OTHER PUBLICATIONS

Morykwas, et al., Extracellular Matric and Healing 1993, pp. 800– Use of Negative Pressure to Increase the Rate of Granulation Tissue Formation in Chronic Open Wounds.
Medical Industry Week—article "KCI Offers New Treatment for Non–Healing Wounds".
Brochure—Hiblow Air Pump.
Brochure—Series 55—Emerson Post–Operative Suction Pumps.
Brochure—Emerson Transport Suction Unit.
Davydov, et al., Vestn. Khir., Sep. 1988—Vacuum Therapy in the Treatment of Acute Suppurative Diseases of Soft Tissues and Suppurative Wounds—(English translation by R. McElroy Translation Co., Austin, Texas).

(List continued on next page.)

Primary Examiner—Weilun Lo
Assistant Examiner—Michael G. Bogart
(74) Attorney, Agent, or Firm—Barnes & Thornburg

(57) ABSTRACT

A bandage for use with a vacuum source includes a wound dressing member to be placed in contact with a wound surface and a suction port associated with the wound dressing member. The member is configured with spacers contacting the wound surface to define suction space between the member and the wound surface. The member also includes holes in communication with the suction space. Passageways of the bandage are provided between the suction port and the holes.

42 Claims, 6 Drawing Sheets

U.S. PATENT DOCUMENTS

| | | |
|---|---|---|
| 2,577,945 A | 12/1951 | Atherton |
| 2,632,443 A | 3/1953 | Lesher |
| 2,682,873 A | 7/1954 | Evans et al. |
| 3,026,874 A | 3/1962 | Stevens |
| 3,315,665 A | 4/1967 | MacLeod |
| 3,367,332 A | 2/1968 | Groves |
| 3,382,867 A | 5/1968 | Reaves |
| 3,520,300 A | 7/1970 | Flower, Jr. |
| 3,528,416 A | 9/1970 | Chamberlain |
| 3,610,238 A * | 10/1971 | Rich, Jr. ............... 128/184 |
| 3,648,692 A | 3/1972 | Wheeler |
| 3,782,377 A | 1/1974 | Rychlik |
| 3,812,972 A | 5/1974 | Rosenblum |
| 3,814,095 A | 6/1974 | Lubens |
| 3,874,387 A | 4/1975 | Barbieri |
| 3,903,882 A | 9/1975 | Augurt |
| 3,935,863 A | 2/1976 | Kliger |
| 3,954,105 A | 5/1976 | Nordby et al. |
| 4,080,970 A | 3/1978 | Miller |
| 4,112,947 A | 9/1978 | Nehring |
| 4,139,004 A | 2/1979 | Gonzalez, Jr. |
| 4,149,541 A | 4/1979 | Gammons et al. |
| 4,224,941 A | 9/1980 | Stivala |
| 4,250,882 A | 2/1981 | Adair |
| 4,275,721 A | 6/1981 | Olson |
| 4,297,995 A | 11/1981 | Golub |
| 4,341,209 A | 7/1982 | Schaar |
| 4,373,519 A | 2/1983 | Errede et al. |
| 4,382,441 A | 5/1983 | Svedman |
| 4,399,816 A | 8/1983 | Spangler |
| 4,457,755 A | 7/1984 | Wilson |
| 4,460,370 A | 7/1984 | Allison et al. |
| 4,465,062 A | 8/1984 | Versaggi et al. |
| 4,469,092 A | 9/1984 | Marshall et al. |
| 4,525,166 A | 6/1985 | Leclerc |
| 4,533,352 A | 8/1985 | VanBeek et al. |
| 4,540,412 A | 9/1985 | Van Overloop |
| 4,553,967 A | 11/1985 | Ferguson et al. |
| 4,569,674 A | 2/1986 | Phillips et al. |
| 4,573,965 A | 3/1986 | Russo |
| 4,579,555 A | 4/1986 | Russo |
| 4,605,399 A | 8/1986 | Weston et al. |
| 4,608,041 A | 8/1986 | Nielsen |
| 4,624,656 A | 11/1986 | Clark et al. |
| 4,633,863 A | 1/1987 | Filips et al. |
| 4,637,819 A | 1/1987 | Ouellette et al. |
| 4,641,643 A | 2/1987 | Greer |
| 4,655,754 A | 4/1987 | Richmond et al. |
| 4,661,093 A | 4/1987 | Beck et al. |
| 4,664,652 A | 5/1987 | Weilbacher |
| 4,667,666 A | 5/1987 | Fryslie |
| 4,679,590 A | 7/1987 | Hergenroeder |
| 4,717,382 A | 1/1988 | Clemens et al. |
| 4,733,659 A | 3/1988 | Edenbaum et al. |
| 4,743,232 A | 5/1988 | Kruger |
| 4,747,166 A | 5/1988 | Kuntz |
| 4,759,354 A | 7/1988 | Quarfoot |
| 4,765,316 A | 8/1988 | Marshall |
| 4,778,446 A | 10/1988 | Jensen |
| 4,778,456 A | 10/1988 | Lokken |
| 4,820,265 A | 4/1989 | DeSatnick et al. |
| 4,820,284 A | 4/1989 | Hauri |
| 4,834,110 A | 5/1989 | Richard |
| 4,872,450 A | 10/1989 | Austad |
| 4,890,608 A | 1/1990 | Steer |
| 4,897,081 A | 1/1990 | Poirier et al. |
| 4,906,240 A | 3/1990 | Reed et al. |
| 4,917,112 A | 4/1990 | Kalt |
| 4,921,492 A | 5/1990 | Schultz et al. |
| 4,941,882 A | 7/1990 | Ward et al. |
| 4,953,565 A | 9/1990 | Tachibana et al. |
| 4,962,761 A * | 10/1990 | Golden ............... 128/400 |
| 4,969,880 A | 11/1990 | Zamierowski |
| 4,969,881 A | 11/1990 | Viesturs |
| 4,988,336 A | 1/1991 | Kohn |
| 4,990,144 A | 2/1991 | Blott |
| 4,991,574 A | 2/1991 | Pocknell |
| 4,997,425 A | 3/1991 | Shioya et al. |
| 5,002,528 A | 3/1991 | Palestrant |
| 5,002,529 A | 3/1991 | Cunningham |
| 5,003,971 A | 4/1991 | Buckley |
| 5,014,389 A | 5/1991 | Ogilvie et al. |
| 5,034,003 A | 7/1991 | Denance |
| 5,034,006 A | 7/1991 | Hosoda et al. |
| 5,042,978 A | 8/1991 | Quenin et al. |
| 5,060,662 A | 10/1991 | Farnswoth, III |
| 5,073,172 A | 12/1991 | Fell |
| 5,086,763 A | 2/1992 | Hathman |
| 5,086,764 A | 2/1992 | Gilman |
| 5,100,396 A | 3/1992 | Zamierowski |
| 5,106,362 A | 4/1992 | Gilman |
| 5,106,629 A | 4/1992 | Cartmell et al. |
| 5,135,518 A | 8/1992 | Vera |
| 5,147,338 A | 9/1992 | Lang et al. |
| 5,149,331 A | 9/1992 | Ferdman et al. |
| 5,152,757 A | 10/1992 | Eriksson |
| 5,160,322 A | 11/1992 | Scheremet et al. |
| 5,167,613 A | 12/1992 | Karami et al. |
| 5,170,781 A | 12/1992 | Loomis |
| 5,176,663 A | 1/1993 | Svedman et al. |
| 5,176,667 A | 1/1993 | DeBring |
| 5,215,539 A | 6/1993 | Schoolman |
| 5,228,431 A | 7/1993 | Giarretto |
| 5,230,350 A | 7/1993 | Fentress |
| 5,261,893 A | 11/1993 | Zamierowski |
| 5,263,922 A | 11/1993 | Sova et al. |
| 5,298,015 A | 3/1994 | Komatsuzaki et al. |
| 5,330,452 A | 7/1994 | Zook |
| 5,344,415 A | 9/1994 | DeBusk et al. |
| 5,349,965 A | 9/1994 | McCarver |
| 5,358,494 A | 10/1994 | Svedman |
| 5,376,252 A | 12/1994 | Ekstrom et al. |
| 5,395,315 A | 3/1995 | Griep |
| 5,431,622 A | 7/1995 | Pyrozyk et al. |
| 5,437,651 A | 8/1995 | Todd et al. |
| 5,445,604 A | 8/1995 | Lang |
| 5,451,215 A | 9/1995 | Wolter |
| 5,478,333 A | 12/1995 | Asherman, Jr. |
| 5,484,427 A | 1/1996 | Gibbons |
| 5,487,889 A | 1/1996 | Eckert et al. |
| 5,527,293 A | 6/1996 | Zamierowski |
| 5,531,670 A | 7/1996 | Westby et al. |
| 5,542,918 A | 8/1996 | Atkinson |
| 5,549,584 A | 8/1996 | Gross |
| 5,556,375 A | 9/1996 | Ewall |
| 5,578,022 A | 11/1996 | Scherson et al. |
| 5,607,388 A | 3/1997 | Ewall |
| 5,628,735 A | 5/1997 | Skow |
| 5,636,643 A | 6/1997 | Argenta et al. |
| 5,645,081 A | 7/1997 | Argenta et al. |
| 5,655,258 A | 8/1997 | Heintz |
| 5,656,027 A | 8/1997 | Ellingboe |
| 5,662,598 A | 9/1997 | Tobin |
| 5,662,624 A | 9/1997 | Sundstrom et al. |
| 5,662,625 A | 9/1997 | Westwood |
| 5,678,564 A | 10/1997 | Lawrence et al. |
| 5,697,920 A | 12/1997 | Gibbons |
| 5,735,833 A | 4/1998 | Olson |
| 5,762,640 A | 6/1998 | Kajiwara et al. |
| 5,782,871 A | 7/1998 | Fujiwara et al. |
| 5,817,145 A | 10/1998 | Augustine et al. |

| | | | | | |
|---|---|---|---|---|---|
| 5,827,246 A | 10/1998 | Bowen | SE | 0084485 | 10/1935 |
| 5,911,222 A | 6/1999 | Lawrence et al. | SU | 587941 | 1/1978 |
| 5,919,476 A | 7/1999 | Fischer et al. | SU | 1268175 A1 | 11/1986 |
| 5,921,972 A | 7/1999 | Skow | WO | WO 89/04158 | 5/1989 |
| 5,928,174 A | 7/1999 | Gibbins | WO | WO 90/11795 | 10/1990 |
| 5,941,859 A | 8/1999 | Lerman | WO | WO 91/00718 | 1/1991 |
| 5,947,914 A | 9/1999 | Augustine | WO | WO 91/16030 | 10/1991 |
| 5,954,680 A | 9/1999 | Augustine | WO | WO 92/19313 | 11/1992 |
| 5,961,480 A | 10/1999 | Augustine | WO | WO 92/20299 | 11/1992 |
| 5,964,721 A | 10/1999 | Augustine | WO | WO 93/09727 | 3/1993 |
| 5,964,723 A | 10/1999 | Augustine | WO | WO 94/00090 | 1/1994 |
| 5,986,163 A | 11/1999 | Augustine | WO | WO 94/20041 | 9/1994 |
| 6,010,527 A | 1/2000 | Augustine et al. | WO | WO 96/05873 | 2/1996 |
| 6,045,518 A | 4/2000 | Augustine | WO | WO 96/15745 | 3/1996 |
| 6,045,541 A | 4/2000 | Matsumoto et al. | WO | WO 99/13793 | 3/1999 |
| 6,071,254 A | 6/2000 | Augustine | WO | WO 00/07653 | 2/2000 |
| 6,071,267 A | 6/2000 | Zamierowski | WO | WO 00/15277 | 3/2000 |
| 6,071,304 A | 6/2000 | Augustine et al. | WO | WO 00/21586 | 4/2000 |
| 6,080,189 A | 6/2000 | Augustine et al. | WO | WO 00/26100 | 5/2000 |
| 6,080,243 A | 6/2000 | Insley et al. | WO | WO 00/30567 | 6/2000 |
| 6,093,160 A | 7/2000 | Augustine et al. | WO | WO 00/32247 | 6/2000 |
| 6,095,992 A | 8/2000 | Augustine | WO | WO 00/38552 | 7/2000 |
| 6,110,197 A | 8/2000 | Augustine et al. | WO | WO 00/38755 | 7/2000 |
| 6,113,561 A | 9/2000 | Augustine | WO | WO 00/42958 | 7/2000 |
| 6,117,111 A | 9/2000 | Fleischmann | WO | WO 00/59418 | 10/2000 |
| 6,135,116 A | 10/2000 | Vogel et al. | WO | WO 00/59424 | 10/2000 |
| 6,142,982 A | 11/2000 | Hunt et al. | WO | WO/0061206 | 10/2000 |
| 6,143,945 A | 11/2000 | Augustine et al. | WO | WO 00/64394 | 11/2000 |
| 6,174,306 B1 | 1/2001 | Fleischmann | WO | WO 01/34223 A1 | 5/2001 |
| 6,203,563 B1 | 3/2001 | Fernandez | WO | WO 01/37922 A2 | 5/2001 |
| 6,207,875 B1 | 3/2001 | Lindqvist et al. | WO | WO 01/49233 A1 | 7/2001 |
| 6,213,965 B1 | 4/2001 | Augustine et al. | WO | WO 01/85248 A1 | 11/2001 |
| 6,213,966 B1 | 4/2001 | Augustine | | | |
| 6,217,535 B1 | 4/2001 | Augustine | | | |
| 6,235,009 B1 | 5/2001 | Skow | | | |
| 6,235,047 B1 | 5/2001 | Augustine et al. | | | |
| 6,241,697 B1 | 6/2001 | Augustine | | | |
| 6,241,698 B1 | 6/2001 | Augustine | | | |
| 6,248,084 B1 | 6/2001 | Augustine et al. | | | |
| 6,254,557 B1 | 7/2001 | Augustine et al. | | | |
| 6,254,580 B1 | 7/2001 | Svedman | | | |
| 6,264,622 B1 | 7/2001 | Augustine | | | |
| 6,264,979 B1 | 7/2001 | Svedman | | | |
| 6,267,740 B1 | 7/2001 | Augustine et al. | | | |
| 6,283,931 B1 | 9/2001 | Augustine | | | |
| 6,284,941 B1 | 9/2001 | Cox et al. | | | |
| 6,290,685 B1 | 9/2001 | Insley et al. | | | |
| 6,293,917 B1 | 9/2001 | Augustine et al. | | | |
| 6,345,623 B1 | 2/2002 | Heaton et al. | | | |
| 6,398,767 B1 * | 6/2002 | Fleischmann ............... 604/313 | | | |
| 6,458,109 B1 * | 10/2002 | Henley et al. .............. 604/340 | | | |
| 2001/0029956 A1 | 10/2001 | Argenta et al. | | | |

FOREIGN PATENT DOCUMENTS

| | | |
|---|---|---|
| EP | 0485657 A1 | 5/1992 |
| EP | 0547496 A1 | 6/1993 |
| EP | 0853 950 A1 | 7/1998 |
| EP | 0 777 504 B1 | 10/1998 |
| EP | 0 880 953 A2 | 12/1998 |
| EP | 1 088 569 A2 | 4/2001 |
| FR | 500253 | 3/1920 |
| FR | 1303238 | 7/1962 |
| GB | 3090 | 6/1902 |
| GB | 641061 | 8/1950 |
| GB | 1 549 756 | 8/1979 |
| GB | 2329127 A | 3/1999 |
| GB | 2333965 A | 8/1999 |
| GB | 2336546 A | 10/1999 |
| GB | 2342584 A | 4/2000 |
| GB | 2344531 A | 7/2000 |
| GB | 2351025 A | 12/2000 |

OTHER PUBLICATIONS

Davydov, et al., Khirurgiia, Jun. 1990—"Pathogenic Mechanism of the Effect of Vacuum Therapy on the Course of the Wound Process" (English translation by R. McElroy Translation Co., Austin, Texas).

Davydov, et al., Vestn. Khir., Nov. 1986—"Vacuum Therapy in the Treatment of Suppurative Lactation Mastitis" (English translation by R. McElroy Translation Co., Austin, Texas).

Davydov, et al., Vestin. Khir., Oct. 1988—"Bacteriological and Cytological Evaluation of the Vacuum Therapy of Suppurative Wounds" (English translation by R. McElroy Translation Co., Austin, Texas).

Davydov, et al., Vestn. Khir., Mar. 1990—"Basis of the Use of Forced Early Secondary Suture in the Treatment of Suppurative Wounds" (English translation by R. McElroy Translation Co., Austin, Texas).

Mirazimov, et al., Ortop Travmatol Protez., Oct. 1966—"Free Skin Graft of the Foot with Preparation of the Wound Surface by Vacuum Treatment" (English translation by R. McElroy Translation Co., Austin, Texas).

Borzov, et al., Vestn. Dermatol. Vernerol., Aug. 1965—"Vacuum Therapy of Some Skin Diseases" (English translation by R. McElroy Translation Co., Austin, Texas).

Jeter et al., Chronic Wound Care: 27: pp. 240–246—"Managing Draining Wounds and Fistulae: New and Established Methods".

Mulder, et al., Wound Healing Publication 1991—"Clinicians' Pocket Guide to Chronic Wound Repair".

Valenta, AIN Apr. 1994; pp. 44–45—"Using the Vacuum Dressing Alternative for Difficult Wounds".

Wolthuis, et al., Physiological Reviews Jul. 1974; vol. 54, No. 3, pp. 566–595—"Physiological Effects of Locally Applied Reduced Pressure in Man".

Fleischmann–WundForum Spezial IHA 1994; pp. 54–55—"Vacuum Sealing for Treatment of Problematical Wounds" (English translation provided).

Bucalo, et al., Wound Repair and Regeneration; Jul.–Sep. 1993; pp. 181–186—"Inhibition of Cell Proliferation by Chronic Wound Fluid".

Olenius, et al., Plastic and Reconstructive Surgery Feb. 19931; pp. 213–215—"Mitotic Activity in Expanded Human Skin".

Viljanto, et al., Br. J. Surg. 1976; vol. 63: pp. 427–430—"Local Hyperalimentation of Open Wounds".

Dunlop, et al., Br. J. Surg. May 1990; vol. 77; pp. 562–563—"Vacuum Drainage of Groin Wounds after Vascular Surgery: A Controlled Trial".

Comment–Dunlop et al., Apr. 1991, pp. 505–506 on "Vacuum Drainage of Groin Wounds after Vascular Surgery".

Landis, et al., Alternate Suction and Pressure, pp. 925–961 — "The Effects of Alternate Suction and Pressure on Blood Flow to the Lower Extremities".

Svedman, et al., Annals of Plastic Surgery Aug. 1986; vol. 17, No. 2: pp. 125–133—"A Dressing System Providing Fluid Supply and Suction Drainage Used for Continuous or Intermittent Irrigation".

Schneider, et al., Plastic and Reconstructive Surgery Sep. 1998, pp. 1195–1198 — "A New and Reliable Method of Securing Skin Grafts to the Difficult Recipient Bed".

Morykwas, et al., www.sma.org/soa/jsoawt97 — "Nonsurgical Modalities to Enhance Healing and Care of Soft Tissue Wounds".

Chariker, et al., Contemporary Surgery Jun. 1989; vol. 34: pp. 59–63 — "Effective Management of Incisional and Cutaneous Fistulae with Closed Suction Wound Drainage".

Tittel, Eingag und Annahme des Manuskripts, Jan. 7, 1987, pp. 104–107 — "New Standards in Postoperative Wound Drainage".

Genecov, et al., Annals of Plastic Surgery Mar. 1998, vol. 40, No. 3: pp. 219–225 — "A Controlled Sub–atmospheric Pressure Dressing Increases the Rate of Skin Graft Donor Site Reepithelialization".

Morykwas, et al., Annals of Plastic Surgery Jun. 1997; vol. 38, No. 6 — "Vacuum–Assisted Closure: A New Method for Wound Control and Treatment: Animal Studies and Basic Foundation".

Argenta, et al., Annals of Plastic Surgery Jun. 1997; vol. 38, No. 6 — "Vacuum–Assisted Closure: A New Method for Wound Control and Treatment: Clinical Experience".

Patent Application and Drawings—"Method of Treating Tissue Damage and Apparatus for Same" consisting of 28 pages.

Patent Application and Drawings — "The Enhancement of Wound Healing and Flap Survival by a New Negative Pressure Device", Argenta et al., consisting of 30 pages.

Nakayama, et al., Ann Plast Surg. May 1991; vol. 26, No. 5: pp. 499–502 — "A New Dressing of Wound Healing and Flap Survival by a New Negative Pressure Device".

Nakayama, et al., Plast. Reconstr. Surg. Dec. 1990; vol. 86 No. 6 pp. 1216–1219 — "A New Method for the Dressing of Free Skin Grafts".

Sames, Br. Med. J. Nov. 5, 1977; vol. 2, No. 6096: 1123 — "Sealing of Wounds with Vacuum Drainage".

Fleishmann, et al., Unfallchirurg, 1993; 96:488–492 — "Vacuum Sealing for Treatment of Soft Tissue Injury in Open Fractures" (English translation of the Summary provided).

Teder, et al., J. of Invest. Surg. 1990; vol. 3: pp. 399–407 — "Continuous Wound Irrigation in the Pig".

Wood, et al., Br. J. of Surg. 1977; vol. 64: pp. 554–557 — "Foam Elastomer Dressing in the Management of Open Granulating Wounds: Experience with 250 Patients".

Neumann, et al., J. of Biomed. Materials Research 1981; vol. 15: pp. 9–18 — "Gelatin–Based Sprayable Foam as a Skin Susbstitute".

Kostluchenok et al., Vestn. Khir. Sep. 1986—"Vacuum Treatment in the Surgical Treatment of Suppurative Wounds" (English translation by R. McElroy Translation Co., Austin, Texas).

Lundvall, et al., Acta. Physiol. Scand. 1989; vol. 136: pp. 403–409 — "Transmission of Externally Applied Negative Pressure to the Underlying Tissue. A Study on the Upper Arm of Man".

Brochure—Aeros—Instavac Aspirator.

Brochure—Pleur–Evac Adult–Pediatric—Non–Metered Disposable "3–Bottle" Unit, A–4000.

Brochure—Aeros—Care–E–Vac.

Brochure—Aeros—Aeros—MoblvacII.

Bochure/Instruction Manual—Creative Medical Laboratories, Inc.—TUGS (Transportable Universal Gradient Suction) System.

Brochure—Wells Johnson Company—Point 5 Aspirator.

Brochure—Microtek Heritage, Inc.—The Wound Evac ET, Closed Wound Suction System.

Brochure—KCI—The V.A.C. (Vacuum Assisted Closure).

Brochure—Augustine Medical, Warm–Up Active Wound Therapy Wound Covers, 1999.

* cited by examiner

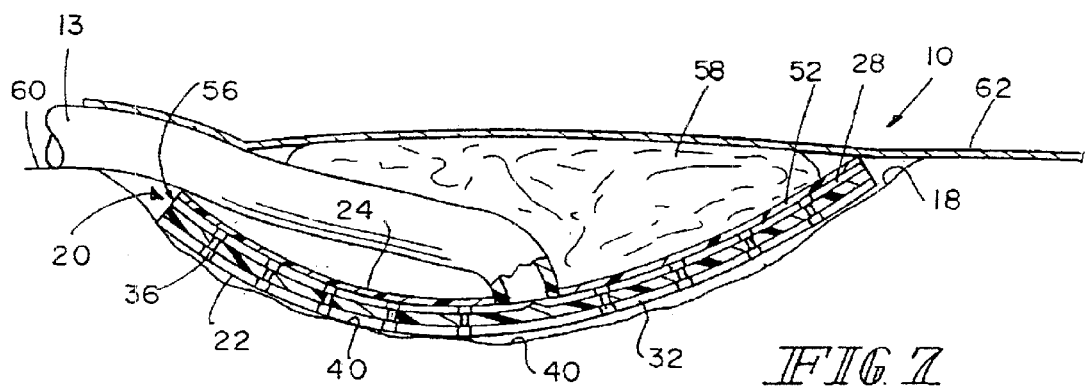
FIG. 7
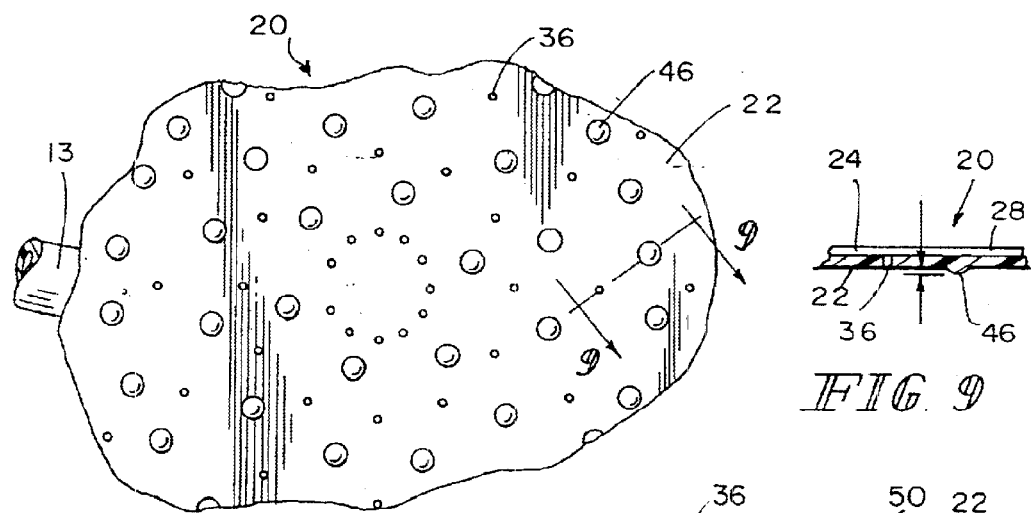
FIG. 8
FIG. 9
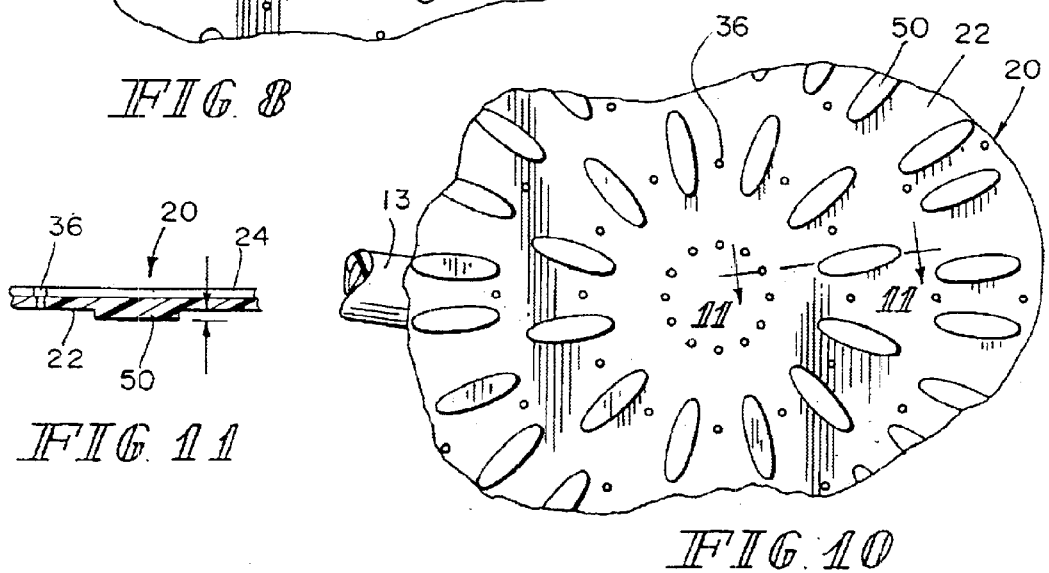
FIG. 11
FIG. 10

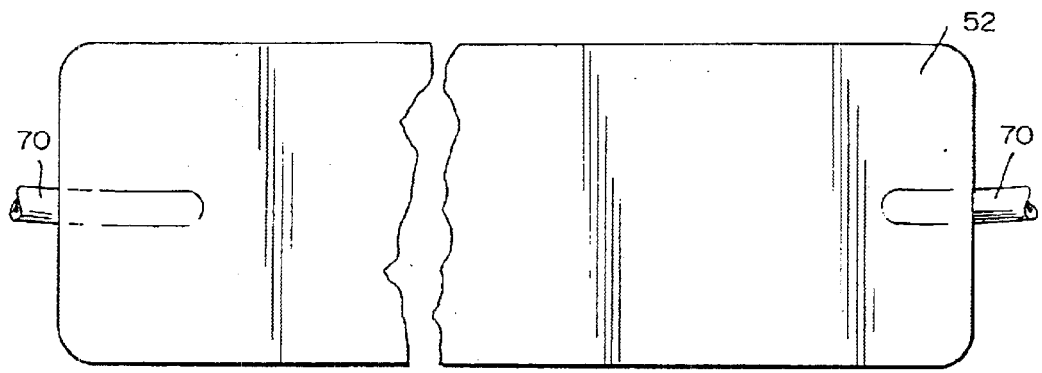
FIG. 12
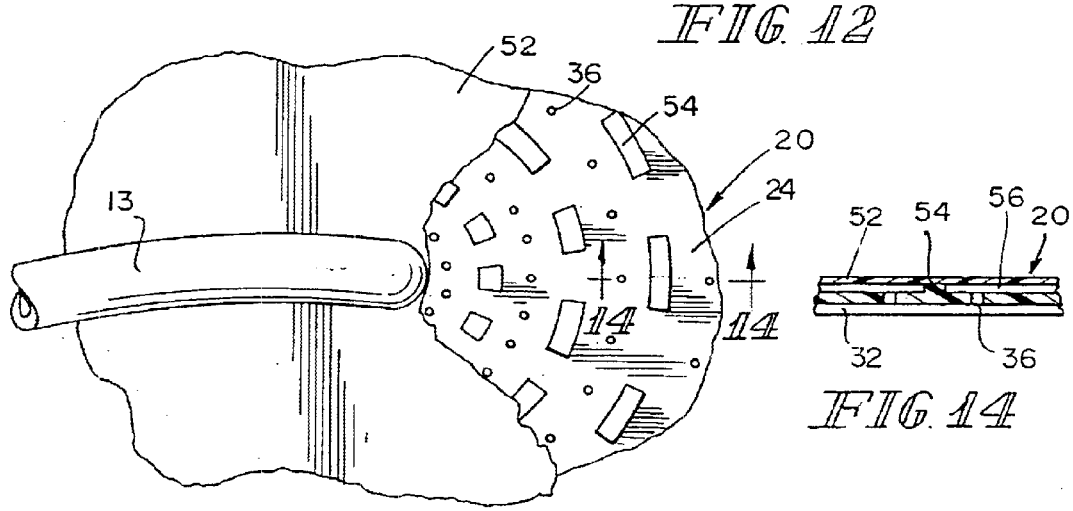
FIG. 13
FIG. 14
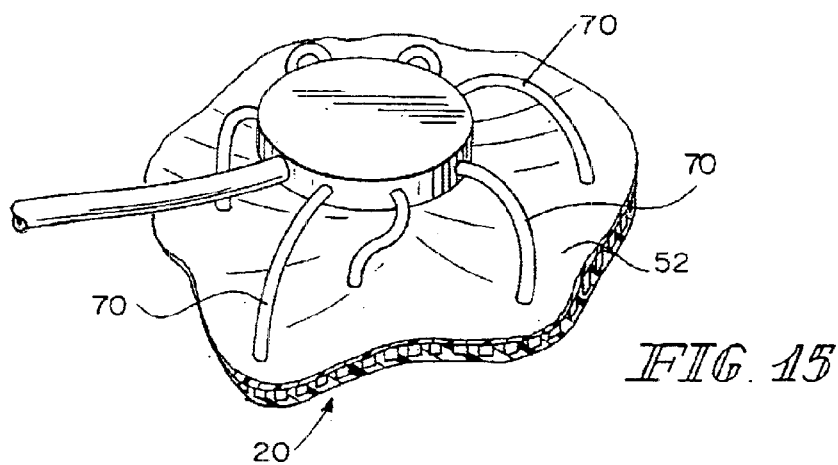
FIG. 15

VACUUM THERAPY AND CLEANSING DRESSING FOR WOUNDS

The present invention relates to bandages for wounds, and more particularly to the provision of bandages for use with a vacuum source.

BACKGROUND AND SUMMARY OF THE INVENTION

The prior art contemplates that chronic wounds may be treated by providing a vacuum in the space above the wound to promote healing.

A number of prior art references teach the value of the vacuum bandage or the provision of the vacuum in the space above the surface of a chronic wound. Several Russian language articles exist which establish the efficacy of vacuum therapy discovered in the 1980s. Examples of such prior art articles, each of which discusses the use of application of vacuum to a wound to promote healing, are as follows: "Vacuum therapy in the treatment of acute suppurative diseases of soft tissues and suppurative wounds", Davydov, et al., Vestn, Khir., September 1988 (The September 1988 article"); "Pathenogenic mechanism of the effect of vacuum therapy on the course of the wound process", Davydov, et al. Khirurigiia, June 1990 ("the June 1990 article"); and "Vacuum therapy in the treatment of suppurative lactation mastitis", Davydov, et al. Vestn. Khir., November 1986 ("the November 1986 article"). The Russian articles distinguish wound drainage from use of vacuum therapy for healing. The Russian authors report that vacuum therapy resulted in faster cleansing of the wound and more rapid detoxification than with the traditional incision-drainage method. The November 1986 Russian article describes the vacuum therapy techniques as a reduction of 0.8–1 atmosphere for 20 minutes at the time of surgery, and subsequent 1.5 to 3 hour treatments at a reduced pressure of 0.1 to 0.15 from atmosphere, twice daily. These Russian articles teach the use of negative pressure to effect healing. The articles describe using several sessions per day, each lasting up to one hour, with a vacuum of 76–114 mmHg. The Russian articles teach using this vacuum method to decrease the number of microbes in the wound. The June 1990 Russian article Leaches that this vacuum therapy provides a significant antibacterial effect. The article describes the stepped up inflow of blood to the zone around the wound to lead to an increase in the number of leukocytes reaching the focus of inflammation. Subsequent articles and patents further develop the benefits obtained with vacuum therapy. The prior art, therefore, teaches the benefit and value of a vacuum bandage.

A vacuum bandage is a bandage having a cover which seals about the outer perimeter of the wound and under which a vacuum is established to act on the wound surface. This vacuum applied to the wound surface causes healing of chronic wounds. Typically, suction tubes are provided for drawing away exudate from the wound, and this suction may be used to create the vacuum under the cover. If the cover is a flexible cover, which is typically more comfortable for the patient, some sort of porous packing may be provided under the cover to provide the space in which the vacuum is formed.

It would be desirable to incorporate in such a bandage a system configured to irrigate the wound surface and to withdraw the irrigation fluids without removal of the bandage. Accordingly, a wound care bandage is provided for use with a vacuum source, the bandage comprising a wound dressing member to be placed in contact with the wound surface. The vacuum source may be any source of vacuum including a vacuum pump and collection canister arrangement to which the bandage is coupled by a tube set. The dressing member either has an access port coupled to it or it is associated with an access port, the port being connected to the vacuum source. The dressing member, which illustratively is a relatively thin and flexible member, has a wound contacting surface and an opposite surface, and a plurality of channels or space providing passageways coupled to the access port to provide communication with areas of the wound surface. The wound contacting surface of the member illustratively includes spacers contacting the wound to define a suction space between the member and the wound surface. The member includes suction holes which communicate with the suction space formed by the spacers. The bandage includes passageways between the port and the suction holes. In some embodiments of the invention, the passageways are provided by a plurality of channels formed in the opposite surface and a cover positioned over the channels.

In some embodiments, the spacers and suction space are defined by a plurality of channels formed in the wound contacting surface. Each of the channels formed in the wound contacting surface opens toward the wound surface and includes side edges contacting the wound.

In some embodiments of the invention, the dressing member has such a plurality of channels formed in patterns on both of the wound contacting surface and the opposite surface and the plurality of holes provide communication between the channels on both surfaces. In some embodiments, the channel patterns on the both surfaces are congruent or superimposed with both patterns radiating outwardly from the port and with the holes spaced radially along the channels.

In some embodiments, the dressing member is made from a material which is to be trimmed conformingly to fit the wound. In some embodiments, the dressing member is relatively transparent such that the condition of the wound surface can be observed through the wound member.

There is provided, therefore, a dressing for a wound, the dressing comprising a relatively thin flexible member which can be trimmed conformingly to fit the wound surface. A suction and irrigation port is associated with the dressing member, and a plurality of channels or passageways is formed in the member leading away from the port to provide communication between the port and areas of the wound surface. The dressing member is provided with a plurality of through holes in communication with the channels. A packing may be placed over the flexible member and a sealing film may be placed over the packing to seal around the perimeter of the wound to provide an enclosed space above the member in which a vacuum is formed by suction on the port. Irrigation fluid may be introduced to the port to impinge upon the wound surface and this fluid and wound exudate is removed from the space between the wound and the bandage member by suction applied to the port. It will be appreciated that the vacuum therapy and the irrigation therapy may take place without removal of the bandage. The illustrative member with the downwardly opening channels or spacers on the wound contacting surfaces provides a suction space which will uniformly apply the vacuum and the irrigation to the surface of the wound bed.

The covered channels on the opposite surface and the holes through the member further contribute to the ability to uniformly apply the vacuum therapy and irrigation fluid to the wound surface. A relatively large portion of the wound surface will be exposed to the vacuum therapy and irrigation using the illustrative bandage member. A large number of redundant passageways are provided for communicating from the access port directly to the wound surface. While some of the passageways may become blocked by exudate particles from the wound surface, other passageways will remain open for suction and irrigation.

The illustrative bandage, therefore, provides a relatively thin, flexible, comfortable bandage member which can be trimmed conformingly to fit into a wound bed and apply vacuum therapy and irrigation uniformly to the wound surface. The illustrative covered channel passageways on the opposite (upper or outer) surface provide a multitude of clearly defined passageways leading from the access port to the through holes leading directly into the suction space under the member.

Features of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 7 is a sectional view of the bandage within the wound of the patient showing the wound surface, the wound contacting surface of the member adjacent the wound surface, the cover adjacent the opposite surface of the member, the tubing coupled to the port of the member, packing, and the outer film coupled to the patient's healthy skin to seal the environment;

FIG. 8 is another embodiment showing an alternate wound contacting surface of the member including spacers for contacting the wound surface to form an open space between the member and the wound surface;

FIG. 9 is a sectional view taken along line 9—9 of FIG. 8 showing one spacer and a through hole of the alternate member;

FIG. 10 is another embodiment showing an another wound contacting surface of the member including spacers or oblong ridges provided to form an open space between the member and the wound surface when the member is placed in the wound;

FIG. 11 is a sectional view taken along line 11—11 of FIG. 10 showing one oblong ridge and through hole of the alternate member;

FIG. 12 is another embodiment showing a wound care bandage having two ports;

FIG. 13 is another embodiment showing an alternate opposite surface of the member having ridges radially spaced around the port to provide a means of flow for exudate being vacuumed from the wound and/or for liquid being dispensed to the wound through the port;

FIG. 15 is yet another embodiment showing a bandage having a plurality of ports each coupled to a vacuum/irrigation tube to provide an evenly distributed suction force across the member.

DETAILED DESCRIPTION OF THE DRAWINGS

Figure 1:
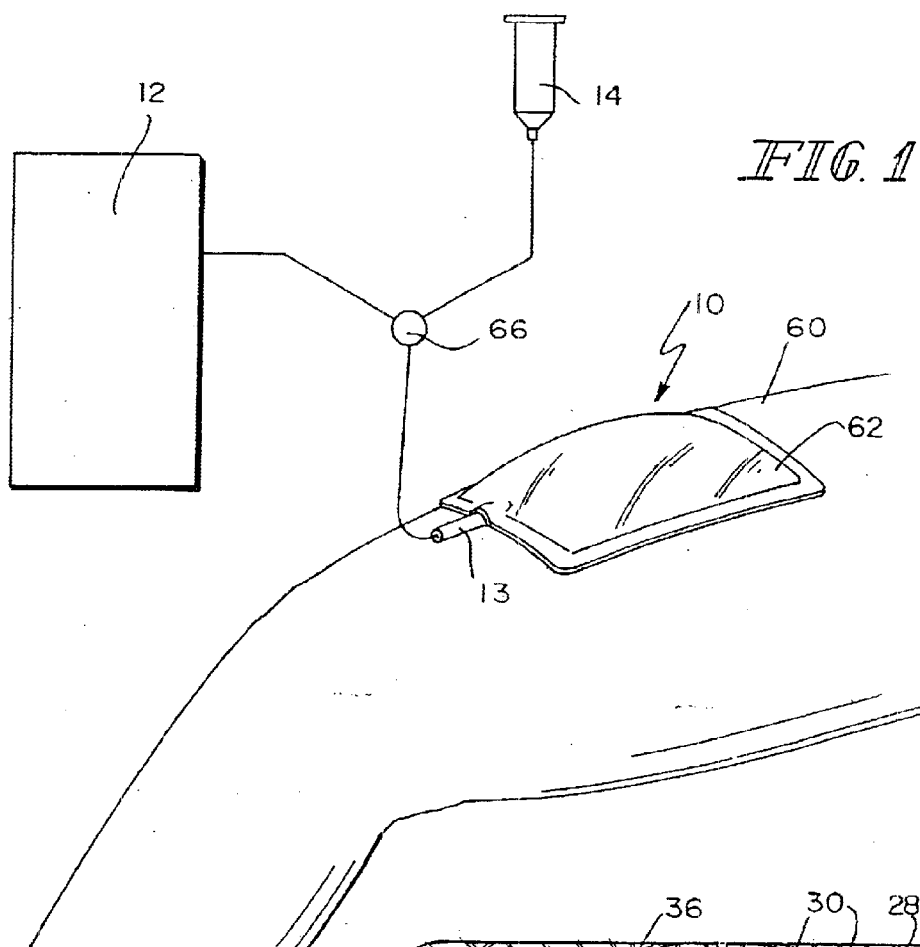
FIG. 1 is a part perspective part diagrammatic view of the wound care bandage showing the wound care bandage located on the leg of a patient and coupled to both a vacuum and an irrigation source through the use of a switch valve.

A wound care bandage 10 is provided for use with a vacuum and irrigation source 12, 14, respectively, as shown in FIG. 1. An illustrative vacuum and irrigation source 12, 14 is disclosed in application Ser. No. 09/725,666 filed simultaneously with this application and assigned to the same assignee. This application is specifically incorporated herein by reference.

Bandage 10 promotes the healing of a large wound 16 (shown in FIGS. 3 and 7) by providing vacuum therapy to the wound 16 to promote blood flow and remove exudate from a wound surface 18 of the wound 16 and by providing for irrigation of the wound 16 with fluids such as saline, for example. Reference is also made to co-pending with this U.S. patent application Ser. No. 09/369,113 filed Aug. 5, 1999 and titled *Wound Treatment Apparatus*. This pending application which is owned by the assignee of this present application is specifically incorporated herein by reference.

Figure 2:
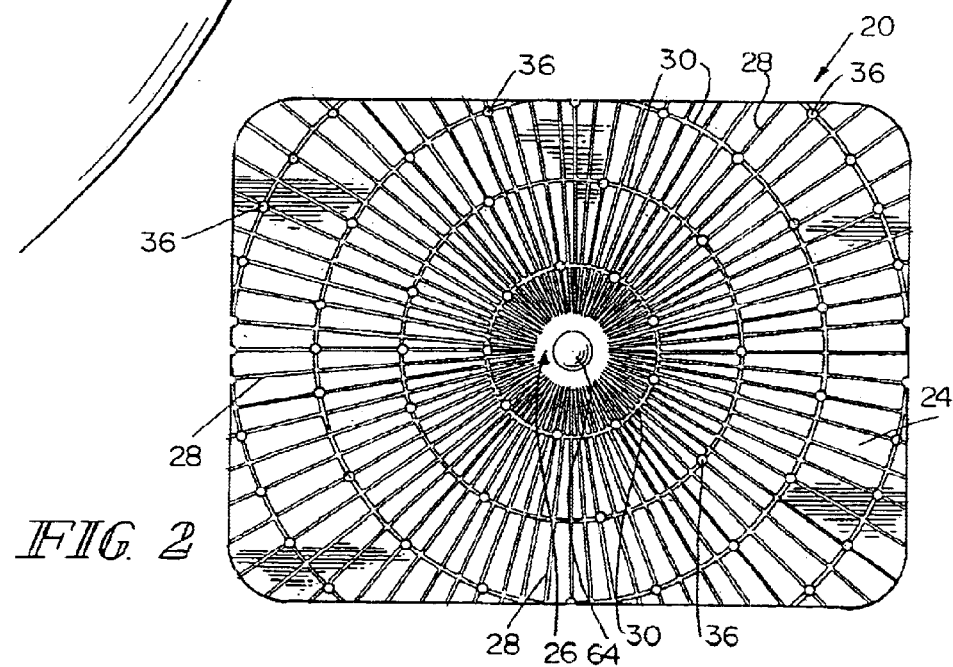
FIG. 2 is a top view of a member of the wound care bandage showing the member including a vacuum/irrigation port, a plurality of channels radiating outwardly from the port, and through holes which extend through the member.
Figure 3:
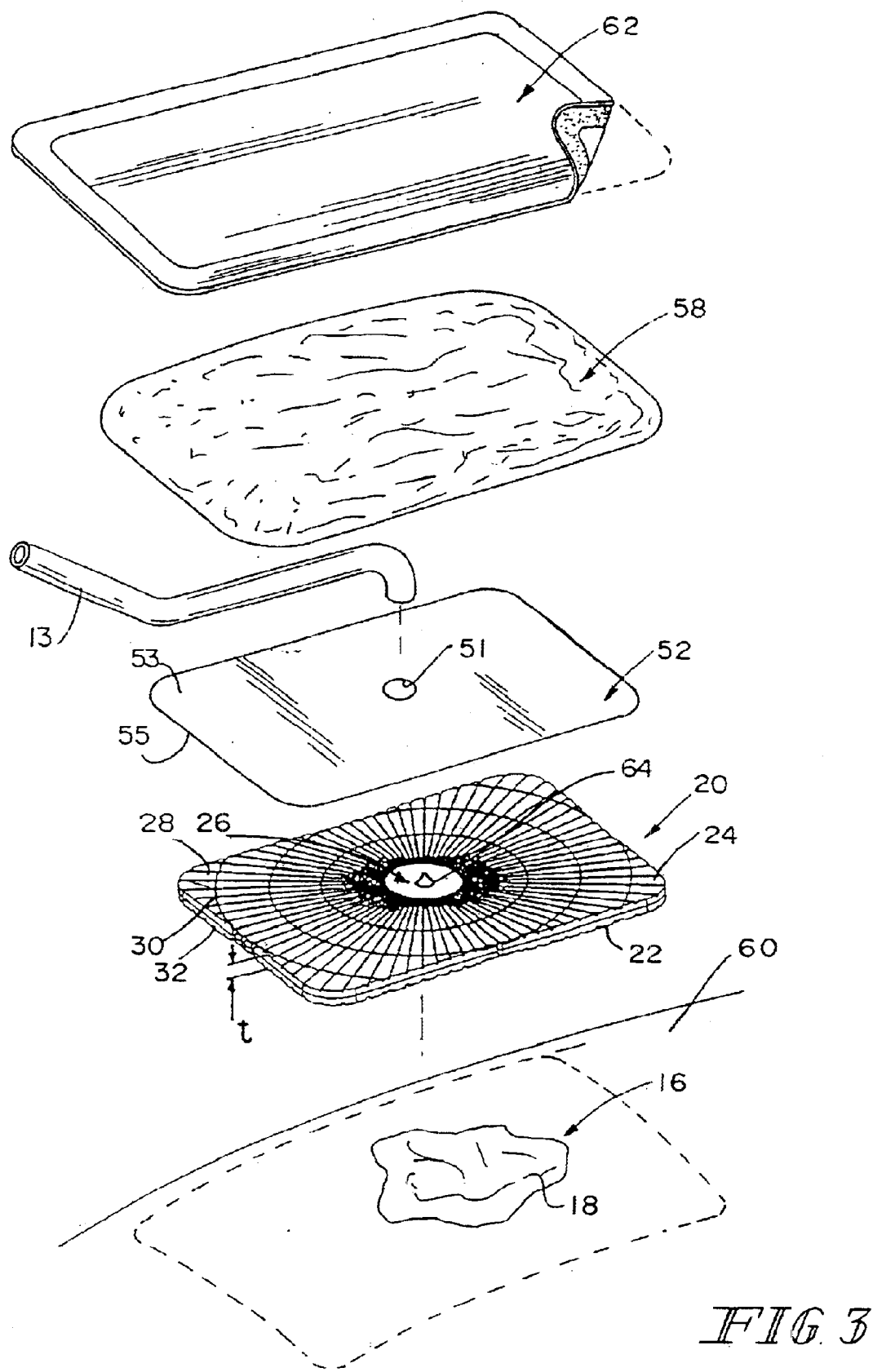
FIG. 3 is an exploded view of one embodiment of the wound care bandage showing the member having a wound contacting surface and an opposite surface, a cover adjacent the opposite surface, tubing which connects to the port of the member at one end and to the vacuum and irrigation sources at another end, packing to be placed on top of the tubing and member, and a sealing film which closes and seals the bandage to allow a vacuum environment to be created.

As shown in FIG. 3, wound care bandage 10 comprises a thin, flexible wound dressing member 20, shown in FIG. 2. Member 20 is made of a medical grade silicone or other type of elastomer which is pliable. Two companies, for example, which manufacture such medical grade silicone are GE Silicones and NuSil Technology. It is within the scope of this disclosure, however, to include a wound dressing member made of any type of thin, flexible material. Member 20 may be molded to include anti-microbial constituents. For example, it is within the scope of this disclosure to impregnate member 20 with silver ions which are known antimicrobials. The following PCT publications illustrate the use of anti-microbials in various products and are incorporated herein by reference: *Antimicrobial Plastic Closures for Drinking Containers*, WO 00/26100; *Antimicrobial Contact Lens Case*, WO 00/038552; *Antimicrobial Fabric and Medical Graft of the Fabric*, WO 00/32247; *Antimicrobial Suturing Ring for Heart Valve*, WO 00/30567.

Figure 4:
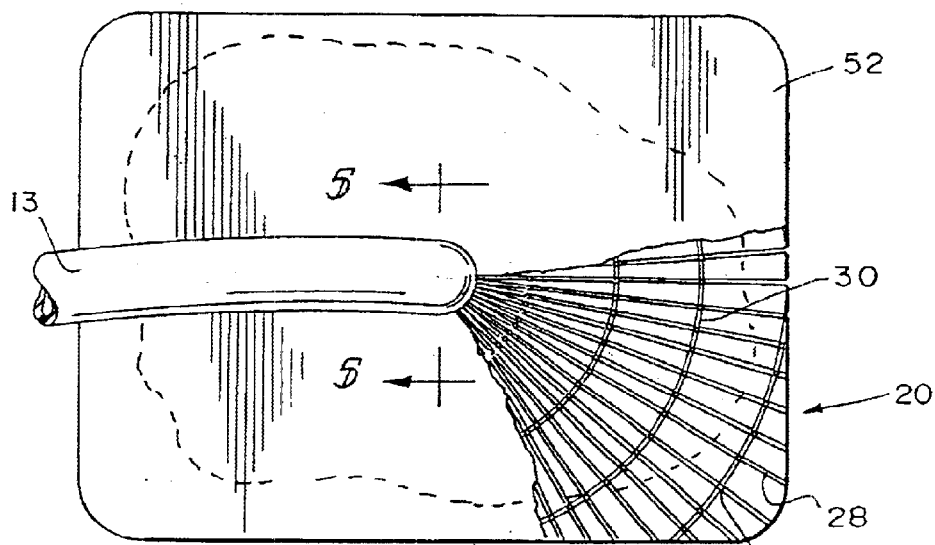
FIG. 4 is a top view of a portion of the bandage showing the cover with portions broken away and showing the member and the channels of the member enclosed by the cover in order to form passageways extending away from the port.
Figure 6:
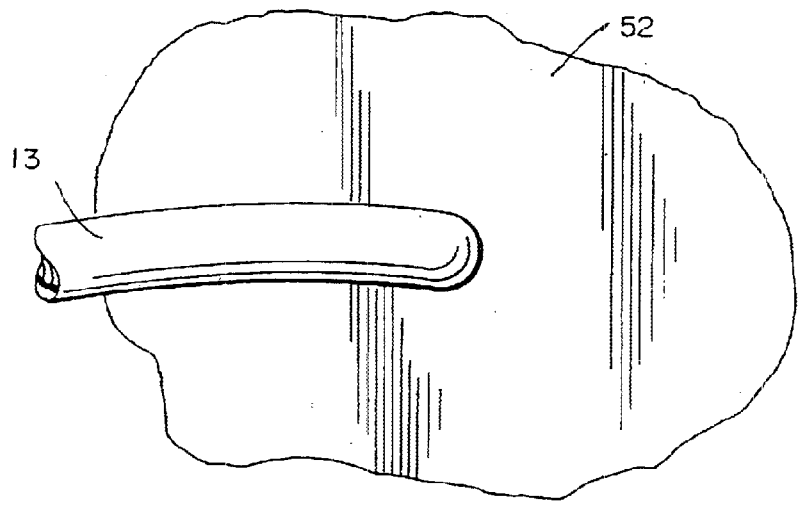
FIG. 6 is a top view of the portion of the member and cover shown in FIGS. 4 and 5 after having been trimmed to fit the particular wound of the patient.

As shown in FIG. 2, wound dressing member 20 is illustratively rectangular in shape. However, it is within the scope of the this disclosure for member 20 to be any suitable shape. Further, member 20 may be cut to fit any size wound 16, as shown in FIGS. 4 and 6. Member 20 is illustratively molded with a thickness of 0.080 inches. Illustratively, member 20 is made from a silicone of a Durometer 50A which is flexible with a thickness of 0.080 inches. It will be appreciated that the channel or passageways formed in the member will further contribute to its flexibility.

Figure 5:
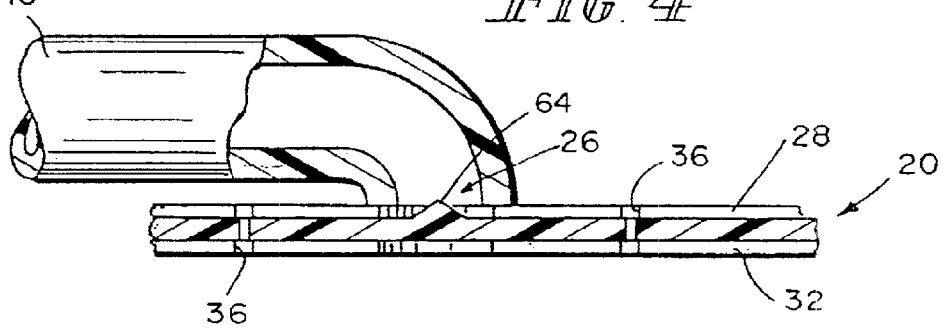
FIG. 5 is a sectional view taken along line 5—5 of FIG. 4 showing the tube which may be sealed to the port, showing a shallow cone of the port, and also showing the channels of the opposite surface and channels of the wound contacting surface and the holes which communicate between the channels.
Figure 16:
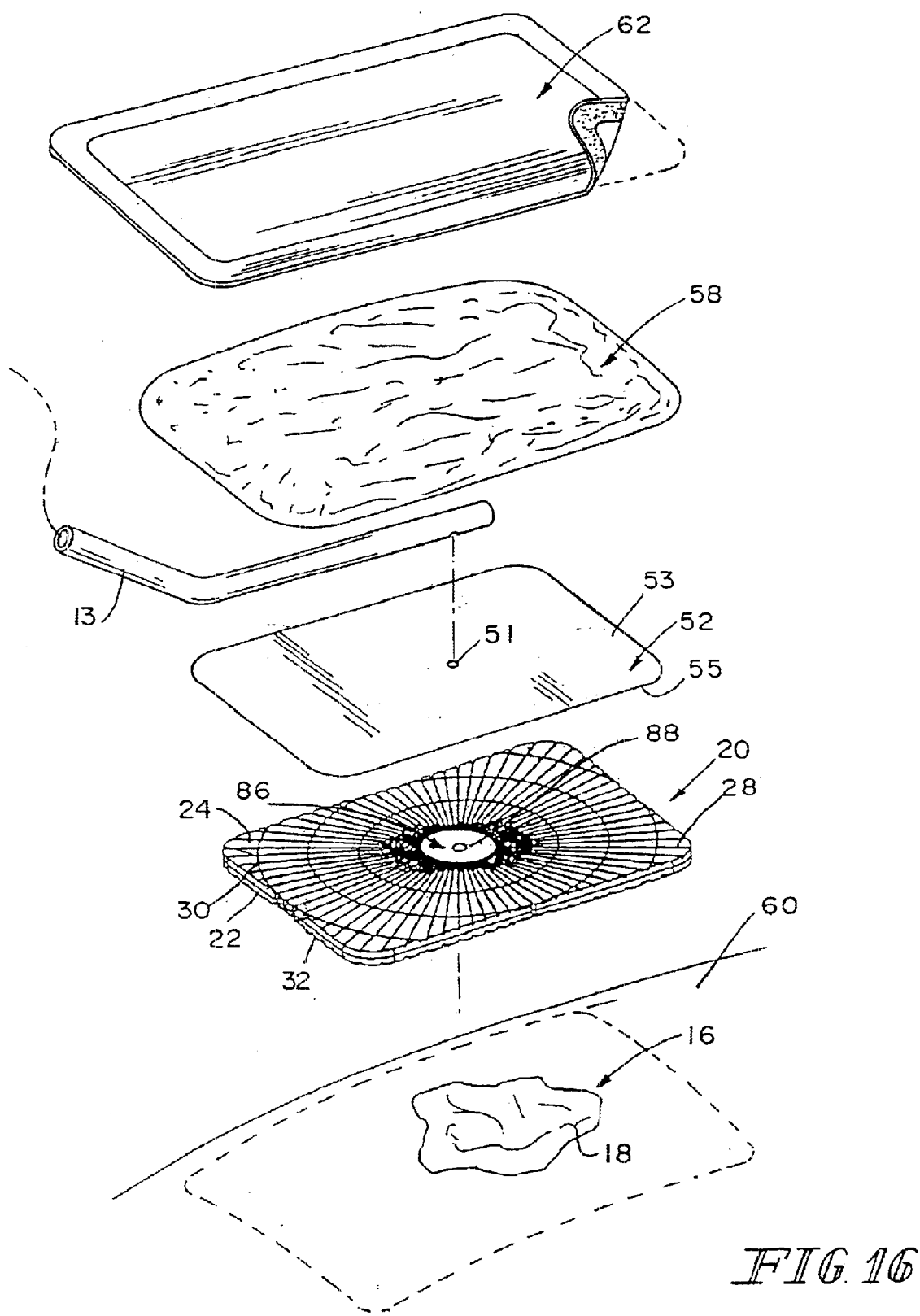
FIG. 16 is another embodiment showing a member of the bandage having a central aperture at the port of the member and channels extending radially outwardly from the central aperture.

Member 20 includes a wound contacting surface 22 and an opposite surface 24. Wound contacting surface 22 or portions thereof contact the wound surface 18 as shown in FIG. 7. Looking to FIG. 2, it can be seen that opposite surface 24 includes a central vacuum/irrigation port 26 and plurality of channels 28 extending radially away from port 26. Illustratively, each channel 28 is 0.030 inches wide and 0.030 inches deep. It is within the scope of the disclosure, however, to include channels 28 of the opposite surface 24 having other width and depth. Port 26, as shown in FIG. 5, includes a shallow cone 64 in order to induce fluids dispensed through a vacuum/irrigation tube 13 from the vacuum and irrigation sources 12, 14 to flow evenly into channels 28. In an alternate embodiment shown in FIG. 16, an alternate port 86 includes an aperture 88 formed through member 20. In the FIG. 16 embodiment, the port communications directly with the suction/irrigation space between the member 20 and the surface of the wound.

Vacuum/irrigation tube 13 is provided coupled to the port. The tube 13 may be molded as part of the member 20 or attached to the member by welding, adhesion or other known techniques. The tube is preferably made of silicone, however, it is within the scope of this disclosure to include a vacuum/irrigation tube made of other medically suited materials. Opposite surface 24 further includes channels 30 which are concentric with port 26, as shown in FIG. 2.

Wound contacting surface 22 includes a plurality of channels 32 which radiate outwardly from the center of member 20 similar to channels 28 of opposite surface 24. Similarly, wound contacting surface 22 also includes a plurality of channels 34 concentric with the center of member 20. Each channel 32, 34 of wound contacting surface 22 opens toward the wound surface 18 and includes outer edges 42 which contact the wound surface 18 or which act as spacers to provide space between the member 20 and the wound surface. Illustratively, the channels 32, 34 of wound contacting surface 22 have the same dimensions as the channels 28, 30 of opposite surface 24. In other words, illustratively channels 32, 34 of wound contacting surface 22 are 0.030 inches deep and 0.030 inches wide. However, it is within the scope of this disclosure to include channels 32, 34 of surface 22 to have other width and depth.

Through holes 36 are provided in member 20 for communication between the channels 28, 30 of the opposite surface 24 with the channels 32, 34 of the wound contacting surface 22. As shown in FIG. 2, holes 36 are illustratively positioned to lie within concentric channels 30, 34 of each respective surface 22, 24 of member 20. Holes 36 are illustratively 0.020 inches in diameter and are illustratively spaced approximately 0.500 inches apart along channels 28, 30 of each respective surface 22, 24. It is, however, within the scope of the disclosure to include holes having other suitable size diameter and other spacing.

Channels 32, 34 of wound contacting surface 22 provide open spaces 40 between the wound surface 18 and member 20, as shown in FIG. 7. Open spaces 40 are defined by each channel 32, 34 of wound contacting surface 22, each outer edge 42 of channels 32, 34, and wound surface 18. Each through hole 36 of member 20 opens into the open spaces 40 formed by channels 32, 34. Open spaces 40 allow vacuum source 12 to establish a generally uniformly distributed vacuum therapy to draw exudate from the wound 16 into the channels 32, 34 of wound contacting surface 22.

It is within the scope of this disclosure to provide spacers 46, for example, shown in FIGS. 8 and 9. Spacers 46 protrude outwardly from wound contacting surface 22 to contact wound surface 18. Open spaces 40 are provided between spacers 46. As shown in FIG. 9, each spacer 46 has an illustrative depth of approximately 0.030 inches. However it is within the scope of this disclosure to include spacers having other suitable dimensions which provide open spaces 40. As with member 20 including channels 32, 34 on wound contacting surface 22, holes 36 of member 20 including spacers 46 are positioned to open into the open spaces 40.

Further, it is within the scope of this disclosure to include member 20 having other types of spacers on wound contacting surface 22 which creates open spaces 40 when wound contacting surface 22 is adjacent the wound surface 18. In another embodiment, as shown in FIGS. 10 and 11, oblong ridges 50 are provided on wound contacting surface 22. Ridges 50 are similar in shape and function to spacers 46. Ridges 50 protrude away from member 20 and contact wound surface 18 when member 20 is place on wound surface 18 to provide open spaces 40 between wound surface 18 and member 20 to establish a generally uniform vacuum across the wound surface 18. As shown in FIG. 11, each ridge 50 illustratively has a preferred depth of 0.030 inches, however, a ridge having other suitable dimensions is within the scope of this disclosure. As illustrated by channels 32, 34 of wound contacting surface 22, spacers 46, or ridges 50, it is within this disclosure to include other structures which acts as spacers to create open spaces 40 between the wound surface 18 and member 20 when member 20 is placed on the wound surface 18 to distribute suction and irrigation generally uniformly throughout the wound 16.

Bandage 10 further comprises a cover 52 for opposite surface 24 of member 20. Cover 52 is provided to cover channels 28, 30 of opposite surface 24. Cover 52 and channels 28 of opposite surface 24 cooperate to form passageways 56, as shown in FIG. 7, extending away from port 26. Passageways 56 are also formed by the cooperation of concentric channels 30 of opposite surface 24 and cover 52. Cover 52 is adhered to member 20 through the use of an adhesive or other suitable means. It will be appreciated that the covered channels 28, 30 provide an ideal way to fabricate a multitude of passageways 56 communicating with the wound surface. In an alternate embodiment, passageways 56 are formed by cooperation of ridges 54 on opposite surface 24 of member 20, rather than channels 30, and cover 52, as shown in FIGS. 13 and 14, for example. It is within the scope of this disclosure to include a bandage 10 forming other passageways 56 extending away from port 26. Holes 36 of member 20 having ridges 54 are located within passageways 56 of bandage 10 similar to holes 36 of member 20 having radial channels 28 and concentric channels 30.

It will be appreciated that the illustrative cover 52 may be provided with scale marking for gauging the wound size or healing progress. Circular markings may be added at 0.5 cm or 1.0 cm intervals to provide convenient measuring of the wound and healing progress.

As shown in FIGS. 3 and 7, bandage 10 further includes gauze or other suitable packing 58 which lies on top of cover 52 and is provided to fill the wound 16 up to the surface of the patient's healthy skin 60. A sealing film 62 of bandage 10 is placed over packing 58. Film 62 is provided to cover the entire wound 16 and to extend across and attach to the patient's healthy skin 60, as shown in FIGS. 1 and 7. Preferably, film 62 is an occlusive or semi-occlusive material which allows water vapor to permeate through. Because of this characteristic, the film 62 is referred to as Moisture Vapor Transmission Rate film or MVTR film. The products Tegaderm™, made by 3M, and OpSite™ by Smith and Nephew can be used for film 62, for example. The product OpSite™ is a semi-permeable film. Film 62 is approximately 0.003 inches thick, however, it is within the scope of this disclosure to include any occlusive or semi-occlusive film 62 having other thickness.

As shown in FIG. 7, vacuum/irrigation tube 13 or an extension added to the tube 13 extends over the edge of member 20 and cover 52 and out from under the edge of the sealing film 62. In use, irrigation source 14 delivers liquid through tube 13 to port 26 and onto the top of a shallow cone 64 of member 20 which extends upwardly as shown in FIGS. 5 and 7. Cone 64 acts to spread the liquid out through the passageways 56 formed by the cooperation of channels 28, 30 (or ridges 54) and cover 52. The fluid moves radially out through passageways 56 to holes 36. The fluid then moved down through holes 36 to open spaces 40 to impinge on wound surface 18.

A switch valve 66 is illustratively provided, as shown in FIG. 1, to allow a user to switch between the use of the vacuum source 12 and the irrigation source 14. It will be appreciated that mechanism other than the switch valve 66 may be used selectively to couple the vacuum source or the irrigation source to the bandage. Simple tube clamps, for example, may be used selectively to open and close the tube set provided with the bandage 10. When valve 66 is switched to operate the vacuum source 12, the vacuum suction draws exudate into the open spaces 40 and up through the holes 36. The exudate is then drawn radially inwardly through passageways 56 toward port 26 and finally through tube 13. Although illustrative bandage 10 includes one central port 26, it is within the scope of this disclosure to include multiple ports 70, as shown in FIGS. 12 and 15, for example. Bandage 10 may make use of two ports 70 located at opposite ends of member 20, as shown in FIG. 12. Alternately, as shown in FIG. 15, bandage 10 may make use of a plurality of ports 70 spaced throughout member 20. It is contemplated that, in some embodiments having two ports, one port may be used for suction or vacuum therapy and the other port may be used for irrigation therapy.

It is contemplated that irrigation source 14 may be operated to provide irrigation fluid at various selected pressures. It is also contemplated that the bandage 10 and dressing member 20 may be provided in various sizes and shapes. The dressing member 20 may be reused with a single patient. It is also contemplated that the dressing 10 may be used with manual irrigation (nurse uses the syringe manually) as well as the powered syringe 14.

Although this invention has been described in detail with reference to certain embodiments, variations and modifications exist within the scope and spirit of the invention as described and defined in the following claims.

What is claimed is:

1. A bandage for use with a vacuum source, the bandage comprising:
   a wound dressing member to be placed in contact with a wound surface, the wound dressing member having spacers contacting the wound surface to define suction space between the wound dressing member and wound surface,
   a suction port associated with the wound dressing member,
   the wound dressing member having suction holes communicating with the suction space, and
   the bandage providing passageways between the suction port and the suction holes.

2. The bandage of claim 1, in which the wound dressing member is a relatively thin, flexible member which can be trimmed conformingly to fit the wound surface, the member having a wound contacting surface providing the spacers and an opposite surface.

3. The bandage of claim 2, in which the passageways are provided by channels formed in the opposite surface leading away from the suction port and a cover over the channels.

4. The bandage of claim 2, in which the passageways are provided by a plurality of channels formed in the opposite surface and a cover over the channels and in which the spacers and suction space are defined by a plurality of channels formed in the wound contacting surface, each channel of the wound contacting surface opens toward the wound surface and includes side edges contacting the wound.

5. The bandage of claim 4, in which the suction holes extend between the channels on the wound contacting surface and the channels on the opposite surface.

6. The bandage of claim 1, in which the bandage is configured to distribute irrigation fluids through the member to the wound dressing wound surface through the suction holes and the suction space.

7. A wound care bandage for use with a vacuum source, the bandage comprising:
   a thin, flexible member to be placed in contact with a wound surface and to be trimmed to fit the wound and provide a space between the member and the wound,
   a plurality of holes to communicate with the space,
   a port associated with the member, and
   passageways extending from the port to the holes.

8. The bandage of claim 7, in which the member includes a wound contacting surface and an opposite surface, the bandage further includes a cover adjacent the opposite surface, an d the passageways are defined by a plurality of channels formed in the opposite surface and the cover.

9. The bandage of claim 7, in which the member includes a wound contacting surface including spacers adapted to contact the wound surface to provide the space between the member and the wound.

10. The bandage of claim 8, in which the opposite surface further includes a plurality of channels concentric with the port and wherein the holes of the bandage are positioned within the concentric channels.

11. The bandage of claim 9, in which spacers are defined by a plurality of channels and each channel includes outer edges which contact the wound surface.

12. A wound care bandage for use with a vacuum source, the bandage comprising:
   a wound dressing member to be placed in direct contact with the wound surface,
   the wound dressing member having at least one access port to be connected to the vacuum source, a wound contacting surface, an opposite surface, and a plurality of channels on the wound contacting surface to provide communication with areas of the wound surface, wherein channels of the wound contacting surface open toward the wound surface.

13. The bandage of claim 12, in which the opposite surface of the wound dressing member includes a plurality of channels extending away from the access port.

14. The bandage of claim 13, in which the wound contacting surface and the opposite surface each include a plurality of additional channels concentric with the access port.

15. The bandage of claim 12, in which the wound dressing member is formed from flexible material conformingly to rest against the wound surface.

16. The bandage of claim 15, in which the wound dressing member is provided with a plurality of holes opening from the opposite surface to the wound contacting surface.

17. The bandage of claim 13, in which the wound dressing member is provided with a plurality of holes opening through the wound dressing member and connecting the channels of the wound contacting surface with the channels of the opposite surface.

18. The bandage of claim 16, in which the holes are in communication with the channels.

19. The bandage of claim 12, in which a plurality of channels is formed on the opposite surface, and the wound dressing member further includes a plurality of holes providing communication between the channels on the wound contacting surface and the channels on the opposite surface.

20. The bandage of claim 19, in which channels on the surfaces radiate away from the access port and with the holes being spaced radially along the channels.

21. The bandage of claim 15, in which the wound dressing member is made from a material which is to be trimmed conformingly to fit the wound.

22. The bandage of claim 19, in which the bandage further includes a cover over the opposite surface to cover the channels on the opposite surface.

23. The invention of claim 12, in which the wound dressing member is formed as a relatively thin, flexible, sheet-like member conformingly to rest against the wound surface, the wound dressing member being provided with a plurality of holes opening through the surface.

24. A dressing for a wound, the dressing comprising:
a relatively thin, flexible member which can be trimmed conformingly to fit the wound surface and which has a wound contacting surface and an opposite surface,
a suction and irrigation port associated with the member,
the wound contacting surface being formed to provide a plurality of spacers to contact the wound surface and position the member to provide space between the member and wound surface in which a vacuum can be established to treat the wound.

25. The dressing of claim 24, in which the member is provided with a plurality of through holes in communication with the space.

26. The dressing of claim 25, in which the plurality of spacers comprises a plurality of channels formed in the wound contacting surface with side edges contacting the wound, the channels of the wound contacting surface opening toward the wound, the through holes being in communication with the channels.

27. The dressing of claim 26, in which the opposite surface is formed to provide a plurality of channels in communication with the port and the holes.

28. The dressing of claim 26, in which the member further includes a plurality of fluid passageways connecting the suction and irrigation port with the holes to the channels formed in the wound contacting surface.

29. The dressing of claim 24, in which the opposite surface includes a plurality of channels in communication with the suction and irrigation port, the spacers on the wound contacting surface are defined by a plurality of channels each having outer edges in contact with the wound surface, and wherein the dressing further includes through holes in communication with the channels on the wound contacting surface and the channels on the opposite surface.

30. The dressing of claim 29, in which the member further includes a plurality of third channels concentric with the suction and irrigation port and wherein the holes are positioned within the third concentric channels.

31. A bandage for use with a vacuum source, the bandage comprising:
a wound dressing member to be placed in contact with a wound surface, the member having spacers contacting the wound surface to define space between the member and wound surface,
a port associated with the member,
the member having holes communicating with the space, and
the bandage providing passageways between the port and the holes.

32. A thin, flexible, sheet-like member for use in a vacuum bandage on a wound surface with the bandage connected to the vacuum source, the member formed to have
a wound contacting surface adapted to be in contact with and conform to the wound surface, and
formed to have a plurality of holes spaced about the wound contacting surface, and the member providing communication from the holes to the vacuum source, wherein a majority of the wound contacting surface is solid.

33. The invention of claim 32, wherein the member is formed of a medical grade material to have passageways providing the communication from the holes to the vacuum source.

34. The invention of claim 33, wherein the wound contacting surface is provided with spacers to define a vacuum space between the wound contacting surface of the member and the wound surface of the wound.

35. The invention of claim 32, wherein the member is transparent.

36. A vacuum bandage for use with a vacuum source, the bandage comprising
a relatively thin, flexible member adapted to be in contact with an open wound and conform to the wound surface, the member having a wound contacting surface formed with a plurality of spaced-apart holes, a port adapted to be attached to the vacuum source, and formed passageways communicating between the holes and the port.

37. The invention of claim 36, wherein the wound contacting surface is provided with spacers to engage the wound surface and provided a vacuum space between the contacting surface and the wound surface.

38. The invention of claim 37, wherein the member is fabricated from a medical grade material.

39. The invention of claim 36, wherein the member is transparent.

40. The invention of claim 36, wherein the formed passageways are channels connecting the port to the holes and wherein the member is fabricated from a medical grade silicone molded to form the port, holes, and channels.

41. A thin, flexible, sheet-like member for use in a vacuum bandage on a wound surface with the bandage connected to the vacuum source, the member comprising:
a wound contacting surface adapted to be in contact with and conform to the wound surface,
a plurality of holes spaced about the wound contacting surface, and the member providing communication from the holes to the vacuum source, and
passageways providing the communication from the holes to the vacuum source, wherein the wound contacting surface is provided with spacers to define a vacuum space between the wound contacting surface of the member and the wound surface of the wound.

42. A vacuum bandage for use with a vacuum source, the bandage comprising a relatively thin, flexible member adapted to be in contact with an open wound and conform to the wound surface, the member having a wound contacting surface formed with a plurality of spaced-apart holes, a port adapted to be attached to the vacuum source, and formed passageways communicating between the holes and the port, wherein the wound contacting surface is provide with spacers to engage the wound surface and provide a vacuum space between the wound contacting surface and the wound surface.

* * * * *